US008847392B2

(12) United States Patent
Endo et al.

(10) Patent No.: US 8,847,392 B2
(45) Date of Patent: Sep. 30, 2014

(54) PANEL-TYPE INPUT DEVICE AND ELECTRONIC APPARATUS HAVING PANEL-TYPE INPUT DEVICE

(75) Inventors: Michiko Endo, Shinagawa (JP); Hideki Iwata, Shinagawa (JP); Fumio Takei, Kawasaki (JP); Takahiro Kashikawa, Kawasaki (JP)

(73) Assignees: Fujitsu Component Limited, Tokyo (JP); Fujitsu Limited, Kawasaki (JP)

( * ) Notice: Subject to any disclaimer, the term of this patent is extended or adjusted under 35 U.S.C. 154(b) by 1040 days.

(21) Appl. No.: 12/320,899

(22) Filed: Feb. 6, 2009

(65) Prior Publication Data

US 2009/0201268 A1    Aug. 13, 2009

(30) Foreign Application Priority Data

Feb. 8, 2008  (JP) .................................. 2008-028965
Jun. 13, 2008  (JP) .................................. 2008-155984

(51) Int. Cl.
*H01L 23/48* (2006.01)
*G06F 3/045* (2006.01)

(52) U.S. Cl.
CPC ..................................... *G06F 3/045* (2013.01)
USPC ......................................................... 257/750

(58) Field of Classification Search
CPC ........... H01L 2924/01029; H01L 2924/01078; H01L 51/0015; H01L 51/0035; G06F 3/045; G06F 3/044; G06F 1/26
USPC ............................................ 257/750; 438/22
See application file for complete search history.

(56) References Cited

U.S. PATENT DOCUMENTS

| 6,045,977 | A | 4/2000 | Chandross et al. |
| 7,781,047 | B2 | 8/2010 | Majumdar et al. |
| 8,007,335 | B2 | 8/2011 | Ohmori et al. |
| 8,018,146 | B2 | 9/2011 | Ohmori et al. |
| 8,068,186 | B2 | 11/2011 | Aufderheide et al. |
| 8,142,688 | B2 | 3/2012 | Kobayashi et al. |
| 2002/0135569 | A1* | 9/2002 | Chen .............................. 345/173 |

(Continued)

FOREIGN PATENT DOCUMENTS

EP    1 986 084 A1    10/2008
JP    2005-182737    7/2005

(Continued)

OTHER PUBLICATIONS

Japanese Office Action mailed Jan. 17, 2012 issued in corresponding Japanese Patent Application No. 2008-155984.

(Continued)

*Primary Examiner* — Duy T Nguyen
(74) *Attorney, Agent, or Firm* — Staas & Halsey LLP

(57) ABSTRACT

A panel-type input device including a pair of electrode plates, each electrode plate having a substrate and a conductive coat provided on a surface of the substrate, the conductive coat of each electrode plate being formed from a conducting polymer. The conductive coat of each electrode plate includes a detecting area adapted to detect a touch input and an inoperative area disposed adjacent to the detecting area, the inoperative area having a surface resistivity higher than a surface resistivity of the detecting area. A parallel electrode pair adapted to apply a voltage to the conductive coat is formed in the detecting area, and conductors connected to the parallel electrode pair are formed in the inoperative area. The inoperative area insulates the conductors from the detecting area.

4 Claims, 12 Drawing Sheets

(56) References Cited

U.S. PATENT DOCUMENTS

| | | |
|---|---|---|
| 2005/0076824 A1 | 4/2005 | Cross et al. |
| 2006/0214156 A1* | 9/2006 | Pan et al. .................. 257/40 |
| 2007/0249088 A1* | 10/2007 | Ohmori et al. .............. 438/99 |

FOREIGN PATENT DOCUMENTS

| | | |
|---|---|---|
| JP | 2005-527048 | 9/2005 |
| JP | 2006-127074 | 5/2006 |
| JP | 2006-185674 | 7/2006 |
| JP | 2006-185675 | 7/2006 |
| JP | 2006-278744 | 10/2006 |
| JP | 2007-508618 | 4/2007 |
| JP | 2007-508639 | 4/2007 |
| JP | 2007-128280 | 5/2007 |
| JP | 2007-272259 | 10/2007 |
| JP | 2008-518397 | 5/2008 |
| KR | 10-2004-0043903 A | 5/2004 |
| KR | 10-2005-0056957 A | 6/2005 |

OTHER PUBLICATIONS

Korean Office Action issued Feb. 25, 2011 in corresponding Korean Patent Application 10-2009-0009566.

Japanese Notice of Reasons for Rejection mailed Jan. 8, 2013, issued in corresponding Japanese Patent Application No. 2012-062707.

Office Action dated Apr. 18, 2013 in corresponding Taiwanese Application No. 098100952.

* cited by examiner

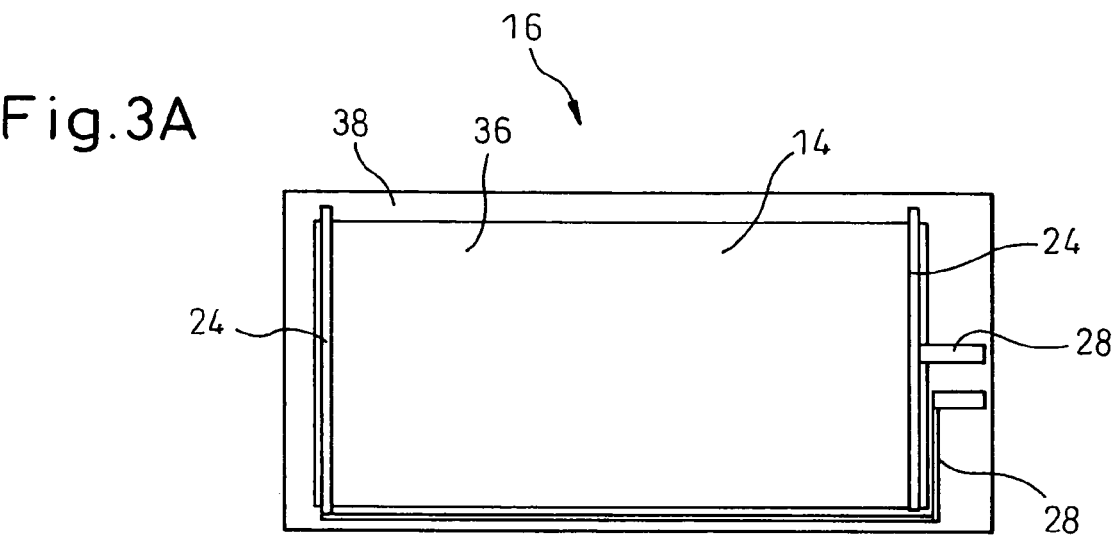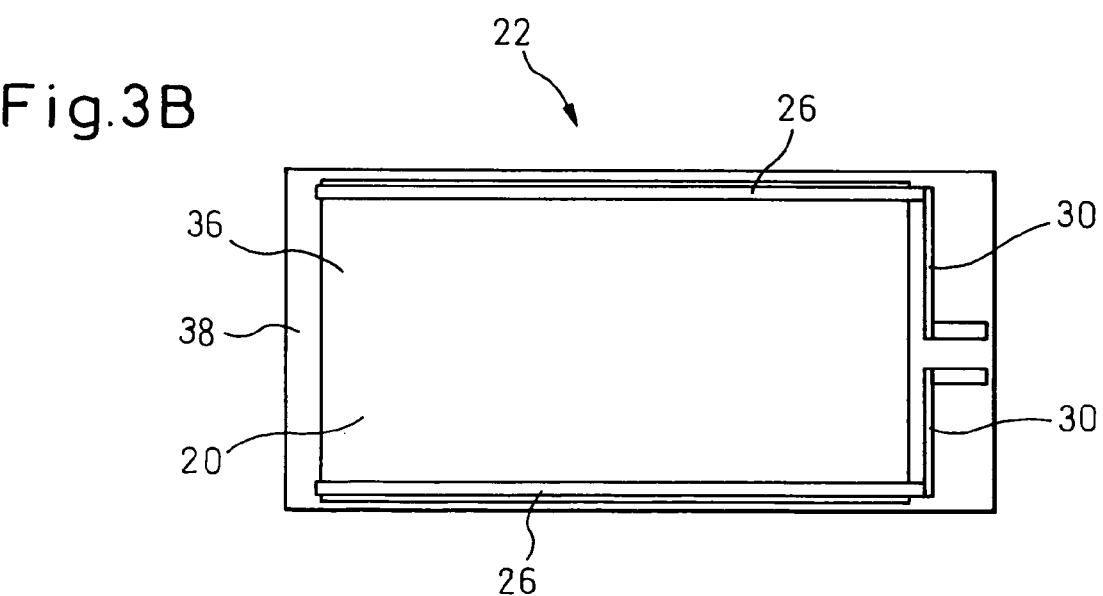

PANEL-TYPE INPUT DEVICE AND ELECTRONIC APPARATUS HAVING PANEL-TYPE INPUT DEVICE

CROSS REFERENCE TO RELATED APPLICATIONS

This application is based on and hereby claims priority to Japanese Patent Application No. 2008-028965 filed Feb. 8, 2008 and Japanese Patent Application No. 2008-155984 filed Jun. 13, 2008.

BACKGROUND OF THE INVENTION

1. Field of the Invention

The present invention relates to a panel-type input device. The present invention also relates to a method of manufacturing a panel-type input device. The present invention further relates to an electronic apparatus having a panel-type input device.

2. Description of the Related Art

A panel-type input device has been known as an input device (or a coordinates detecting device) of an electronic apparatus including a display unit, such as a personal computer, a personal digital assistant (PDA), an automatic teller machine (ATM), etc., which is operated to indicate two-dimensional coordinate data in the display unit by an operator touching a desired point on a panel surface with his or her finger or with a pen. In particular, a panel-type input device with a transparent structure which can be mounted on a screen of a display unit, such as a liquid crystal display (LCD), a plasma display panel (PDP), a cathode ray tube (CRT), etc., has been widely used as a so-called touch panel, and in recent years, has been realized as an input device to be installed in a portable terminal unit having a mobile-phone function.

A resistive-type touch panel, as one example of a panel-type input device, includes a pair of transparent electrode plates, each having a transparent insulating substrate and a transparent conductive coat provided on one surface of the substrate, and has a configuration wherein the electrode plates are assembled with each other in such a relative arrangement that the conductive coats are opposed to and spaced from each other while permitting a conductive contact therebetween. As input-coordinates detection systems provided for the resistive-type touch panel, an analog system in which the conductive coat of each electrode plate is configured to be uniformly formed over the generally entire surface of the substrate, and a digital system in which the conductive coat of each electrode plate is configured to be divided into a plurality of strip-shaped portions on the surface of the substrate, have been known.

In the analog system, each electrode plate is generally provided, in a region extending along an outer edge of the electrode plate, with a pair of positive and negative strip-shaped electrodes (hereinafter referred generically as a parallel electrode pair) formed on the conductive coat so as to be parallel to and spaced from each other, and conductors are formed on an insulating layer on the conductive coat so as to be connected to the parallel electrode pair. Voltages are applied to the conductive coats of the mutually opposing electrode plates, via the conductors and the parallel electrode pairs, in directions orthogonal to each other. In this state, when an operator presses a desired point of one of the electrode plates (i.e., performs a touch input) so as to make the conductive coats of the mutually opposing electrode plates come into local conductive contact with each other, a divided voltage corresponding to the resistance value of the respective conductive coats is measured at the pressed point, and a coordinate of the pressed point is thereby detected.

In the digital system, a pair of electrode plates are combined with each other and positioned relative to each other in such a manner that the respective sets of strip-shaped portions of the respective conductive coats extend in directions orthogonal to each other. Voltages are applied to the sets of strip-shaped portions of the respective conductive coats of the mutually opposing electrode plates, and when an operator presses a desired point of one of the electrode plates (i.e., performs a touch input) so as to make the strip-shaped portions of the conductive coats of the mutually opposing electrode plates come into conductive contact with each other at the intersection thereof, the input operation at the intersection is detected.

A capacitive-type touch panel, as another example of a panel-type input device, includes a transparent electrode plate having a transparent insulating substrate and a transparent conductive coat provided on one surface of the substrate. As input-coordinates detection systems provided for the capacitive-type touch panel, a surface capacitive system in which the conductive coat of the electrode plate is configured to be uniformly formed over the generally entire surface of the substrate, and a projected capacitive system in which the conductive coat of the electrode plate is configured to be divided into a plurality of strip-shaped portions on the surface of the substrate, have been known.

In the surface capacitive system, the touch panel is essentially constructed by using only a single electrode plate. A uniform electric potential is given to the conductive coat by electrodes provided at four corners of the conductive coat. When an operator touches a desired point of the electrode plate (i.e., performs a touch input) with a finger, an electric current is generated at the touched point, and a coordinate of the touched point is detected based on the ratio between current values obtained at the four corner electrodes.

In the projected capacitive system, the touch panel is constructed by using a single electrode plate or a pair of opposing electrode plates, in which a pair of conductive coats, each being divided into a plurality of strip-shaped portions, are disposed on the opposite surfaces of the single electrode plate or on the mutually opposing surfaces of the opposing electrode plates, in such a manner that the conductive coats are opposed to and insulated from each other and the respective sets of strip-shaped portions of the conductive coats extend in directions orthogonal to each other. Voltage is applied to the respective sets of strip-shaped portions of the conductive coats. When an operator touches a desired point of the electrode plate (i.e., performs a touch input) with a finger, an electric current is generated at the touched point, or an electrostatic capacity between the mutually opposing conductive coats changes at the touched point, and a coordinate of the touched point is detected based on the locations of the strip-shaped portions generating electric currents correspondingly to distances from the touched point.

In a conventional panel-type input device as described above, the conductive coat is generally formed on the surface of the substrate by a coat-forming technology, such as vacuum deposition, sputtering, etc., using a metal oxide such as an indium tin oxide (ITO). On the other hand, in recent years, a panel-type input device provided with a conductive coat formed from an electrically conductive polymer (hereinafter referred to as a conducting polymer) has been proposed. For example, Japanese Unexamined Patent Publication (Kokai) No. 2005-182737 (JP-A-2005-182737) discloses an analog-system based resistive-type touch panel provided with a conductive coat formed from a transparent conducting polymer. Japanese Unexamined Patent Publication (Kokai) No. 2005-527048 (JP-A-2005-527048) also discloses a capacitive-type touch panel provided with a conductive coat formed from a transparent conducting polymer. JP-A-2005-527048 discloses both a surface capacitive system and a projected capacitive system. In any of the conventional panel-type input devices, the conductive coat formed from the conducting polymer has advantages, as compared to an ITO coat, in that the conducting polymer is excellent in impact resistance, writing durability, etc., and can be formed by a simple process such as coating or printing.

As described above, a conventional panel-type input device is provided, in connection with the conductive coat formed on the surface of the substrate, with an electrically insulating region having a predetermined profile formed on the surface of the same substrate or on the surface of the conductive coat. For example, in an analog-system based resistive-type touch panel, an insulating layer having a predetermined profile, on which conductors or connectors connected to the parallel electrode pair are disposed, is formed on the conductive coat along the outer edge of the substrate by, e.g., coating or printing. Alternatively, an insulating region for disposing conductors or connectors may be formed along the outer edge of the substrate by locally removing a part of the conductive coat through etching or the like. In a digital-system based resistive-type touch panel, or a projected-capacitive-system based capacitive-type touch panel, a plurality of strip-shaped portions of the conductive coat as well as an insulating region insulating the strip-shaped portions from each other are formed by locally removing, through etching or the like, a part of the conductive coat uniformly formed on the surface of the substrate.

The process for forming the insulating layer on the conductive coat through coating or printing requires a material for the insulating layer, and increases the entire thickness of the panel-type input device due to the thickness of the insulating layer. On the other hand, the process for forming the insulating region by locally removing the conductive coat through etching or the like requires the provision of a coating removing apparatus such as etching equipment and the increased number of processing steps, which may raise the manufacturing cost of the panel-type input device. In particular, in a touch panel adapted to be mounted on a screen of a display unit and configured such that the insulating region formed by locally removing the conductive coat exists within an area superimposed on the screen, the difference of the thickness or light transmission between the strip-shaped portion (i.e., a detecting area) and the insulating region (i.e., an inoperative area) may allow a boundary line between the strip-shaped portion and the insulating region to be visible or the detecting area and the inoperative area to be visually distinguishable, which may degrade the visibility of the display screen through the touch panel.

SUMMARY OF THE INVENTION

It is an object of the present invention to provide a panel-type input device equipped with a conducting polymer used as a conductive coat, which can reduce a panel thickness and can form an insulating region at a desired position with a desired pattern at low cost.

It is another object of the present invention to provide a method of manufacturing a panel-type input device equipped with a conducting polymer used as a conductive coat, which can reduce a panel thickness and can form an insulating region at a desired position with a desired pattern at low cost.

It is still another object of the present invention to provide an electronic apparatus including a panel-type input device equipped with a conducting polymer used as a conductive coat, which can reduce a panel thickness and can form an insulating region at a desired position with a desired pattern at low cost.

It is a still further object of the present invention to provide a panel-type input device configured as a touch panel and a method of manufacturing the panel-type input device, which can eliminate drawbacks, such that a boundary line between a detecting area and an inoperative area may be visible or a detecting area and an inoperative area may be visually distinguishable, and thus can improve the visibility of a display screen through the panel-type input device.

To accomplish the above object, the first aspect of the present invention provides a panel-type input device comprising a pair of electrode plates, each electrode plate having a substrate and a conductive coat provided on a surface of the substrate, the conductive coat of each electrode plate being formed from a conducting polymer, the pair of electrode plates being assembled with each other in a relative arrangement such that conductive coats of the electrode plates are opposed to and spaced from each other while permitting a conductive contact between the conductive coats; wherein the conductive coat of each electrode plate comprises a detecting area adapted to detect a touch input and an inoperative area disposed adjacent to the detecting area, the inoperative area having a surface resistivity higher than a surface resistivity of the detecting area; wherein a parallel electrode pair adapted to apply a voltage to the conductive coat is formed in the detecting area, and conductors connected to the parallel electrode pair are formed in the inoperative area; and wherein the inoperative area insulates the conductors from the detecting area.

The second aspect of the present invention provides a panel-type input device comprising a pair of electrode plates, each electrode plate having a substrate and a conductive coat provided on a surface of the substrate, the conductive coat of each electrode plate being formed from a conducting polymer, the pair of electrode plates being assembled with each other in a relative arrangement such that conductive coats of the electrode plates are opposed to and spaced from each other while permitting a conductive contact between the conductive coats; wherein the conductive coat of each electrode plate comprises a plurality of detecting areas adapted to detect a touch input and an inoperative area disposed adjacent to the plurality of detecting areas, the inoperative area having a surface resistivity higher than a surface resistivity of the plurality of detecting areas and insulating the plurality of detecting areas from each other; and wherein the plurality of detecting areas of the conductive coat of each electrode plate extend parallel to each other, and respective sets of the plurality of detecting areas of the conductive coats of the pair of electrode plates extend in directions intersecting with each other.

The third aspect of the present invention provides a panel-type input device comprising a pair of conductive coats disposed oppositely to and insulated from each other, each conductive coat being formed from a conducting polymer; wherein each conductive coat comprises a plurality of detecting areas adapted to detect a touch input and an inoperative area disposed adjacent to the plurality of detecting areas, the inoperative area having a surface resistivity higher than a surface resistivity of the plurality of detecting areas and insulating the plurality of detecting areas from each other; and wherein the plurality of detecting areas of each conductive coat extend parallel to each other, and respective sets of the plurality of detecting areas of the pair of conductive coats extend in directions intersecting with each other.

In the above panel-type input device, the pair of conductive coats may be provided on mutually opposing surfaces of a pair of substrates disposed oppositely to each other; and an insulating layer may be interposed between the pair of conductive coats. Alternatively, the pair of conductive coats may be provided on opposite surfaces of a single substrate.

In the above panel-type input device, an auxiliary conductive layer formed from an inorganic conducting substance may also be provided between the detecting areas and the surface of the substrate.

In the above several aspects of the panel-type input device, the conducting polymer forming the conductive coat may contain an additive adapted to be denatured into either one of an oxidizing substance and a basic substance by ultraviolet light irradiation; and the pair of conductive coats may be transparent.

The other aspect of the present invention provides an electronic apparatus comprising a display unit; and the aforementioned panel-type input device including the pair of transparent conductive coats, the panel-type input device being mounted on a screen of the display unit.

A further aspect of the present invention provides a method of manufacturing the aforementioned panel-type input device, comprising the steps of providing a pair of electrode plates, each electrode plate having a substrate and a conductive coat provided on a surface of the substrate, the conductive coat of each electrode plate being formed from a conducting polymer; setting a mask having a shielding portion and a transmitting portion over the conductive coat of each electrode plate; and irradiating the conductive coat with ultraviolet light through the transmitting portion of the mask, or alternatively, contacting the conductive coat with a conductivity controlling agent containing either one of an oxidizing substance and a basic substance through the transmitting portion of the mask, so as to increase a surface resistivity of one region of the conductive coat corresponding to the transmitting portion to an extent higher than a surface resistivity of another region of the conductive coat corresponding to the shielding portion, and to form the detecting area and the inoperative area in the conductive coat of each electrode plate.

A yet further aspect of the present invention provides a method of manufacturing the aforementioned panel-type input device, comprising the steps of providing a pair of conductive coats, each conductive coat being formed from a conducting polymer; setting a mask having a shielding portion and a transmitting portion over each conductive coat; and irradiating the conductive coat with ultraviolet light through the transmitting portion of the mask, or alternatively, contacting the conductive coat with a conductivity controlling agent containing either one of an oxidizing substance and a basic substance through the transmitting portion of the mask, so as to increase a surface resistivity of a region of the conductive coat corresponding to the transmitting portion to an extent higher than a surface resistivity of another region of the conductive coat corresponding to the shielding portion, and to form the plurality of detecting areas and the inoperative area in each conductive coat.

BRIEF DESCRIPTION OF THE DRAWINGS

The above and other objects, features and advantages of the present invention will become more apparent from the following description of preferred embodiments in connection with the accompanying drawings, wherein:

FIG. 3A is a plan view showing a first electrode plate of the panel-type input device show in FIG. 1;

FIG. 3B is a plan view showing a second electrode plate of the panel-type input device shown in FIG. 1;

DESCRIPTION OF THE PREFERRED EMBODIMENT

Figure 1:
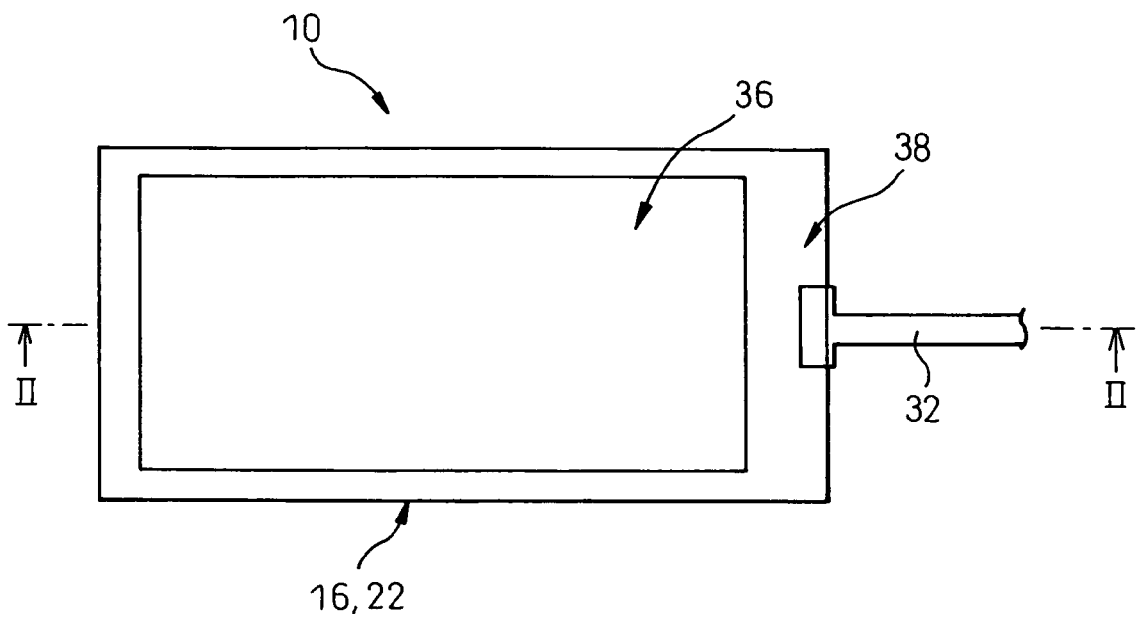
FIG. 1 is a plan view schematically showing a panel-type input device according to a first embodiment of the present invention.

The embodiments of the present invention are described below in detail with reference to the accompanying drawings. In the drawings, same or similar components are denoted by common reference numerals.

Figure 2:
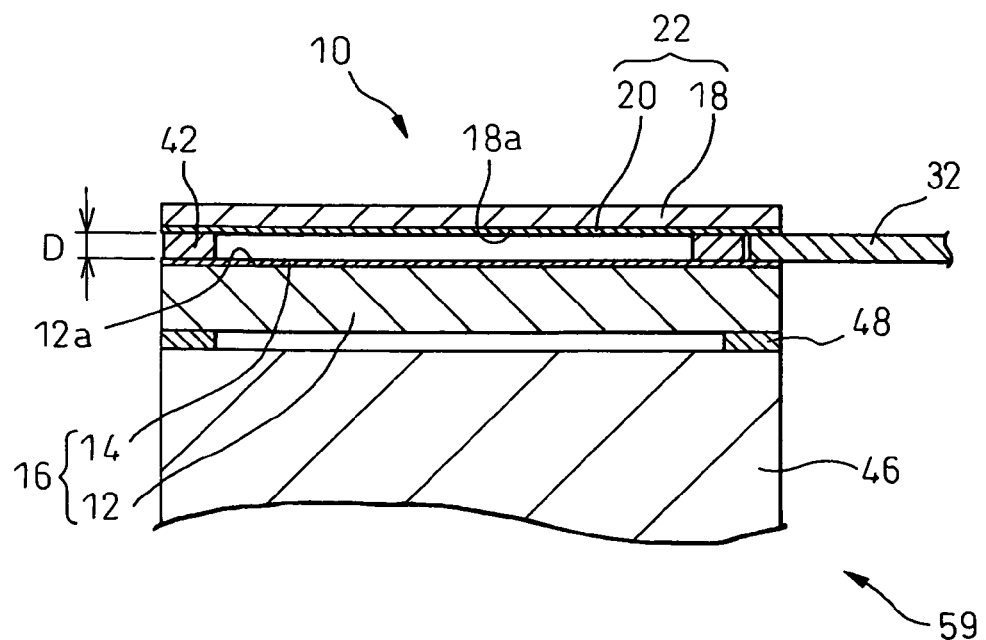
FIG. 2 is a sectional view schematically showing an electronic apparatus according to an embodiment of the present invention, which includes the panel-type input device shown in FIG. 1, and taken along a line II-II of FIG. 1.
Figure 4:
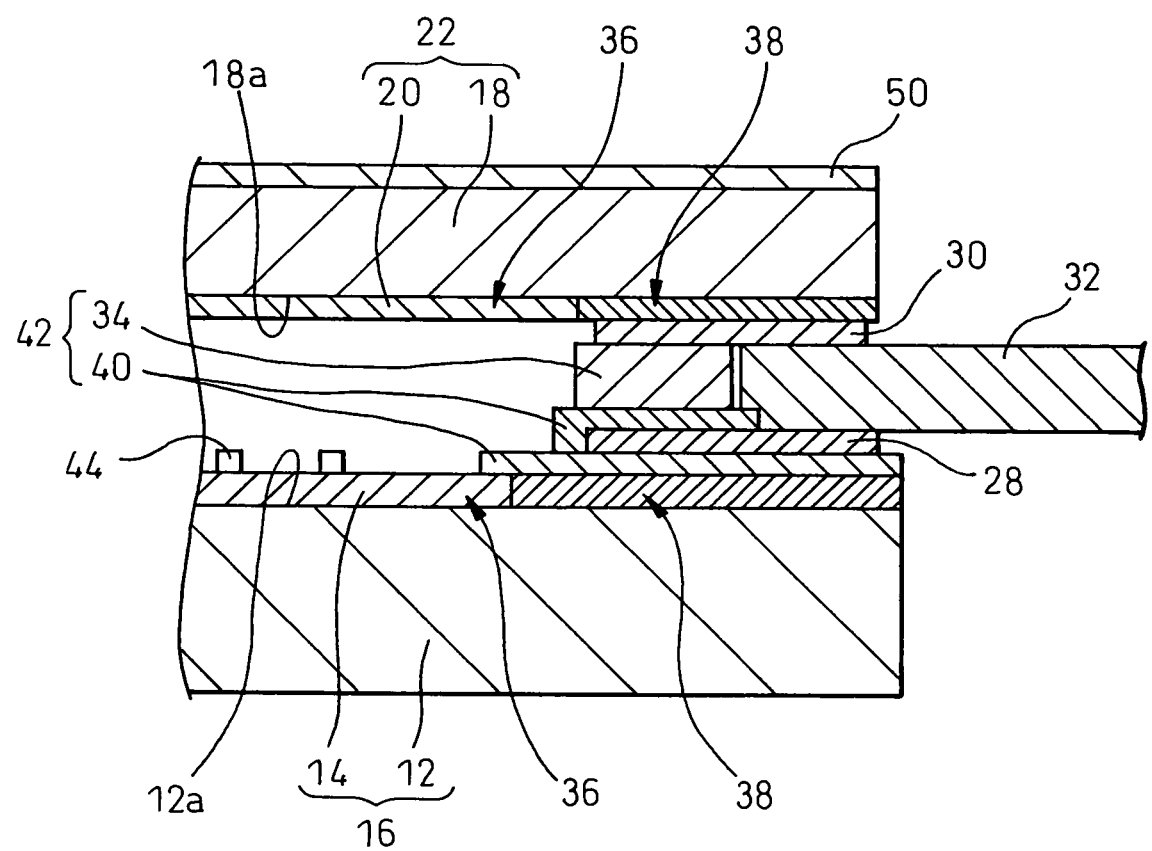
FIG. 4 is an enlarged schematic sectional view showing a part of the panel-type input device shown in FIG. 1.

Referring to the drawings, FIG. 1 is a plan view schematically showing a panel-type input device 10 according to a first embodiment of the present invention; FIG. 2 is a schematic sectional view of the panel-type input device 10; FIG. 3 is a plan view schematically showing components of the panel-type input device 10; and FIG. 4 is an enlarged sectional view schematically showing a part of the panel-type input device 10. The panel-type input device 10 has a configuration applicable to an analog-system based resistive-type touch panel.

The panel-type input device 10 includes a first electrode plate 16 having a first electrical-insulating substrate 12 and a first electrical-conductive coat 14 provided on a surface 12a of the first substrate 12, and a second electrode plate 22 having a second electrical-insulating substrate 18 and a second electrical-conductive coat 20 provided on a surface 18a of the second substrate 18 (FIG. 2). The first substrate 12 and first conductive coat 14 of the first electrode plate 16 and the second substrate 18 and second conductive coat 20 of the second electrode plate 22 have rectangular profiles generally identical to each other as seen in a plan view.

A pair of strip-shaped, positive and negative first electrodes (i.e., a first parallel electrode pair) 24 is provided on the first conductive coat 14 of the first electrode plate 16 at a location along a pair of opposing sides of the rectangular profile, and patterned and laminated directly on the first conductive coat 14 through, e.g., a screen printing, so as to be electrically connected to the first conductive coat 14 (FIG. 3A). Similarly, a pair of strip-shaped, positive and negative second electrodes (i.e., a second parallel electrode pair) 26 is provided on the second conductive coat 20 of the second electrode plate 22 at a location along another pair of opposing sides of the rectangular profile, different from the location of the first parallel electrode pair 24, and patterned and laminated directly on the second conductive coat 20 through, e.g., a screen printing, so as to be electrically connected to the second conductive coat 20 (FIG. 3B).

A pair of first conductors 28 individually connected to the first parallel electrode pair 24 is provided on the first electrode plate 16 in a state where the first conductors 28 are insulated from the first conductive coat 14, and is patterned into a predetermined profile through, e.g., screen printing. Similarly, a pair of second conductors 30 individually connected to the second parallel electrode pair 26 is provided on the second electrode plate 22 in a state where the second conductors 30 are insulated from the second conductive coat 20, and is patterned into a predetermined profile through, e.g., screen printing. The first and second conductors 28, 30 are collected at predetermined locations on the respective electrode plates 16, 20, and connected to a connector (e.g., a flexible printed circuit board) 32 constituting an interface with a not-shown control circuit (FIGS. 1, 2 and 4).

The first electrode plate 16 and the second electrode plate 22 are assembled with each other in a relative arrangement such that the first and second conductive coats 14, 20 are opposed to and spaced from each other while permitting a conductive contact therebetween, and are fixed to each other in a mutually superposed state by an electrical-insulating adhesive layer (e.g., a double-sided adhesive tape) 34 (FIG. 4) having a strip shape (a rectangular frame shape, in the illustrated embodiment) and provided along the outer edges of the mutually opposing conductive coats 14, 20. In this assembly, the first and second conductive coats 14, 20 are disposed at positions where their respective profiles are substantially aligned with each other, and the first and second parallel electrode pairs 24, 26 connected respectively to the first and second conductive coats 14, 20 are disposed at positions different or rotated from each other by 90 degrees.

In the panel-type input device 10, each of the first and second conductive coats 14, 20 of the first and second electrode plate 16, 22 is formed by using an electrically conductive polymer (i.e., a conducting polymer). One example of the conducting polymer that can be preferably used for the first and second conductive coats 14, 20 is, e.g., a polythiophene-based conducting polymer as described in JP-A-2005-182737. In particular, in the case where the panel-type input device 10 is configured as a touch panel having a transparent structure, the polythiophene-based polymer is preferred in excellent transparency. Other conducting polymers that can be used in the panel-type input device 10 are polyaniline, polypyrrole, polyethylene dioxythiophene (PEDOT), etc. Thickness of each conductive coat 14, 20 formed from the conducting polymer is not particularly limited, but preferably is in the range of 0.01 µm to 10 µm, and more preferably is in the range of 0.1 µm to 1 µm. If the thickness is less than 0.01 µm, electrical resistance of each conductive coat 14, 20 may become unstable, and if thickness is more than 10 m, adhesiveness relative to each substrate 12, 18 may be degraded.

The panel-type input device 10 according to the present invention has a characteristic configuration in which each of the first and second conductive coats 14, 20 formed from the conducting polymer includes a single detecting area 36 adapted to detect a touch input and an inoperative area 38 disposed adjacent to the detecting area 36, the inoperative area 38 having a surface resistivity higher than a surface resistivity of the detecting area 36. In the illustrated embodiment, the inoperative area 38 is formed in the shape of a rectangular or picture frame along the outer edge of each conductive coat 14, 20, and the detecting area 36 having a rectangular profile is formed inside the inoperative area 38 so as to occupy most of each conductive coat 14, 20. The parallel electrode pair 24, 26 adapted to apply a voltage to each conductive coat 14, 20 is formed in the detecting area 36, and the conductors 28, 30 connected to the parallel electrode pair 24, 26 are formed in the inoperative area 38. In this configuration, the inoperative area 38 acts to insulate the conductors 28, 30 from the detecting area 36. In order to ensure the insulating properties, it is sufficient that the surface resistivity (pursuant to, e.g., JIS K6911) of the detecting area 36 of each conductive coat 14, 20 is set as, e.g., 500Ω/□ (ohm/square) to 1000Ω/□ while the surface resistivity of the inoperative area is set as, e.g., at least 10000Ω/□.

The adhesive layer 34 is disposed along the inoperative area 38 of the conductive coat 14, 20 of each electrode plate 16, 22 and, together with an auxiliary insulating layer 40, constitutes an intermediate layer 42 extending in a strip shape (a rectangular frame shape, in the illustrated embodiment) along the outer edges of the first and second electrode plates 16, 22 (FIG. 4). The intermediate layer 42 functions as a spacer defining and ensuring a spacing distance D between the conductive coats 14, 20 of the first and second electrode plates 16, 22 (FIG. 2). A plurality of electrical-insulating dot spacers 44 are provided in a suitably dispersed arrangement within the detecting area 36 on the conductive coat 14, 20 (the first conductive coat 14, in the drawing) of either one of the first and second electrode plates 16, 22 (the first electrode plate 16, in the drawing) (FIG. 4). The dot spacers 44 act to suppress an unintended concave flexure of the respective electrode plates 16, 22 due to, e.g., their own weight, so as to keep a gap between the mutually opposing conductive coats 14, 20 and, when either one of the electrode plates 16, 22 deforms under a pressing force, to allow a local contact between the mutually opposing conductive coats 14, 20 at a pressed point.

The panel-type input device 10 operates, under the control of a control circuit (not shown), by applying a predetermined voltage alternately to the first parallel electrode pair 24 and the second parallel electrode pair 26, connected respectively to the first conductive coat 14 of the first electrode plate 16 and the second conductive coat 20 of the second electrode plate 22. In this state, at the instant when an operator presses a desired point on the outer surface of, e.g., the second substrate 18 of the second electrode plate 22 with a pen or a finger, etc. (i.e., performs a touch input), the conductive coats 14, 20 come into conductive contact with each other at the pressed point, and a divided voltage corresponding to a resistance value of each conductive coat 14, 20 determined by the position of the pressed point is outputted from one of the conductive coats 14, 20 to which a voltage is not applied. A processing section (not shown) provided in the control circuit measures the divided voltage alternately generated in the conductive coats 14, 20, and thereby detects a two-dimensional coordinate of the pressed point.

The panel-type input device 10 may be configured as a touch panel having a transparent structure, which can be mounted to be superposed on a screen of a display unit, such as a liquid crystal display (LCD), a plasma display panel (PDP), a cathode ray tube (CRT), etc. (FIG. 2). Alternatively, the panel-type input device 10 may be configured as an opaque or translucent structure known as a pointing device. The panel-type input device 10 configured as a transparent touch panel may have an exemplary configuration such that the first electrode plate 16 is used as a lower-side electrode plate disposed adjacent to the screen of a display unit with an adhesive layer 48 interposed therebetween, and that the first substrate 12 thereof is formed from a transparent glass or resin plate or a transparent resin film and the first conductive coat 14 is formed from a transparent conducting polymer. The second electrode plate 22 may also be used as an upper-side electrode plate subjected to a pressing operation by an operator, the second substrate 18 thereof may be formed from a transparent resin film with high flexibility, and the second conductive coat 20 may be formed from a transparent conducting polymer. Resinous materials suitable for the first and second substrate 12, 18 are polycarbonate, acryl, polyethylene terephthalate (PET), etc.

The panel-type input device 10 configured as a touch panel may further include an auxiliary functional layer 50 acting to, e.g., protect a resinous film material or improve visibility of a display screen, on the outer surface of the second substrate 18 of the second electrode plate 22 (FIG. 4). The second substrate 18 made of a transparent resin film may also be formed from a PET film having ultraviolet protection properties, and/or the auxiliary functional layer 50 may be formed from a material having ultraviolet protection properties, so that it is possible to manufacture a touch panel possessing excellent resistance to ultraviolet radiation, which can protect the first and second conductive coats 14, 20 (especially, the detecting areas 36 thereof) against ultraviolet radiation such as sunlight during use of a finished product of the touch panel. The ultraviolet protection properties can be obtained by adding an ultraviolet absorbing agent, such as oxybenzene, octyl methoxycinnamate, mexoryl, octocrylene, to the material.

Figure 5:
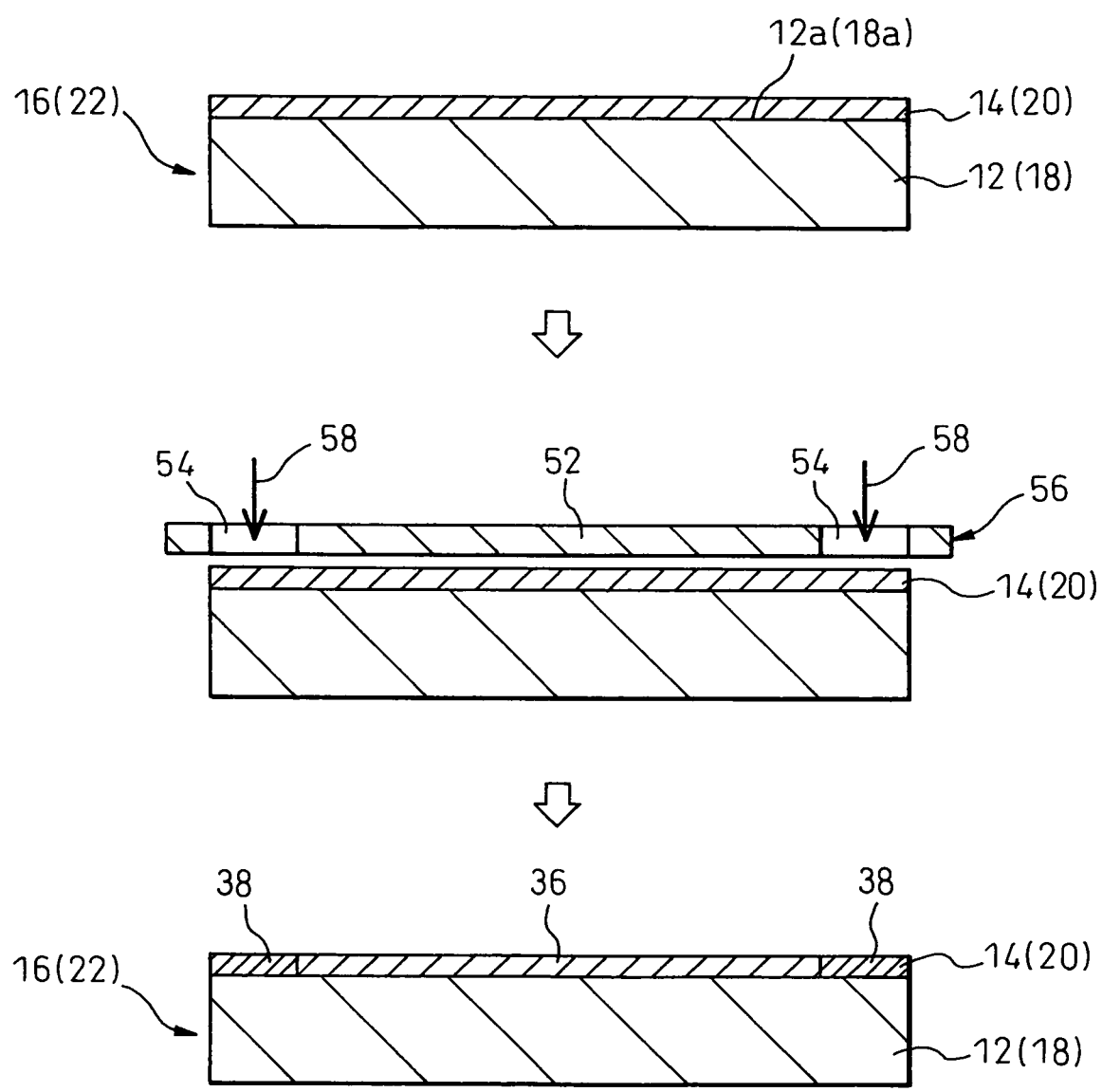
FIG. 5 is an illustration for explaining major steps of a manufacturing method, according to an embodiment of the present invention, for manufacturing the panel-type input device shown in FIG. 1.
Figure 6:
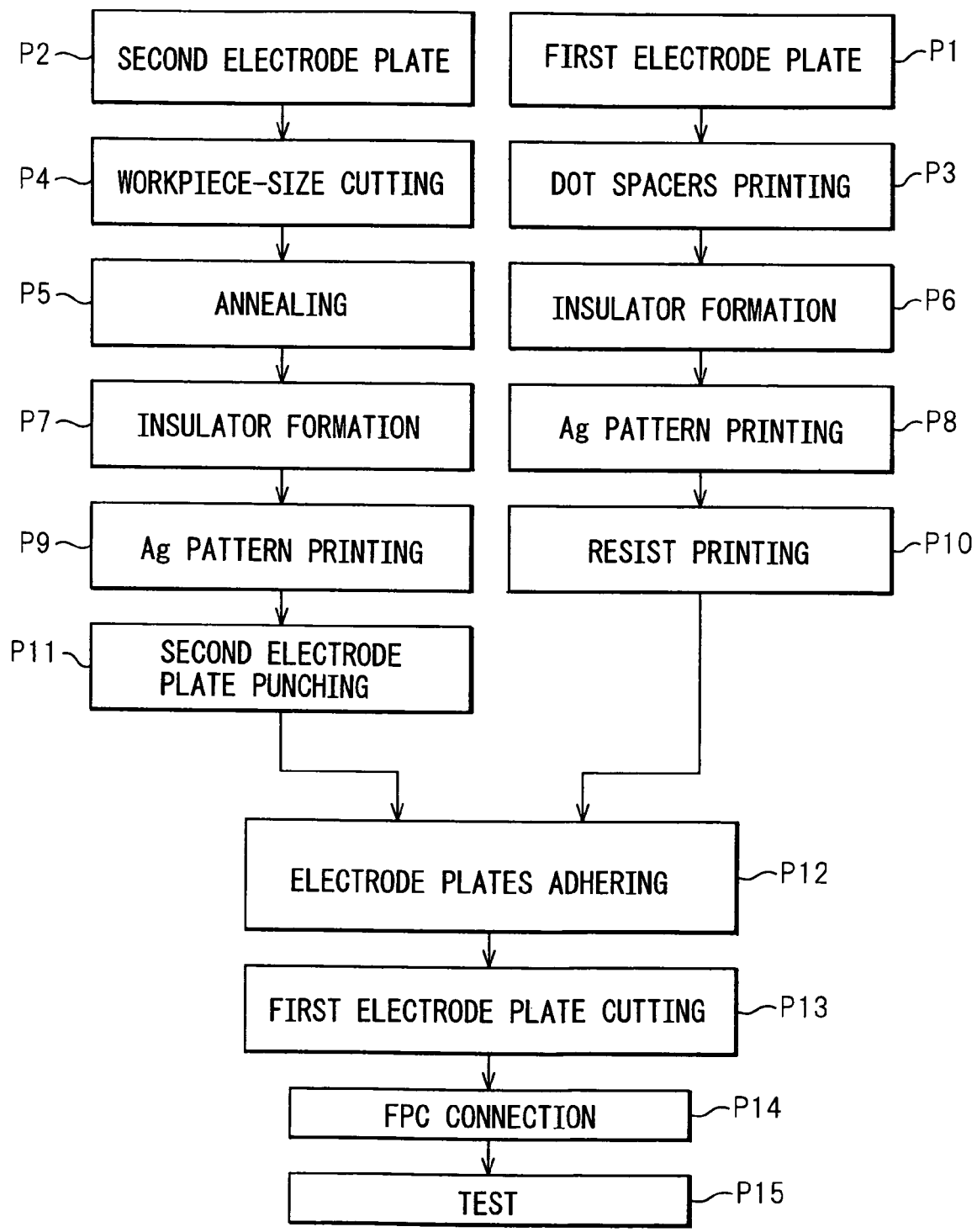
FIG. 6 is a flow chart showing the manufacturing method and including the steps shown in FIG. 5.

An exemplary method of manufacturing the panel-type input device 10 will be described below with reference to the schematic view of FIG. 5 and the flow chart of FIG. 6. First, a first electrode plate 16 with a first conductive coat 14 formed or laminated on the surface 12a of a first substrate 12 and a second electrode plate 22 with a second conductive coat 20 formed or laminated on the surface 18a of a second substrate 18 are provided (steps P1 and P2). Process of forming the conductive coats 14, 20 made of a conducting polymer is not particularly limited, but a coating process such as spin coating, roller coating, bar coating, dip coating, gravure coating, curtain coating, die coating, spray coating, doctor coating, kneader coating, etc., or a printing process such as screen printing, spray printing, inkjet printing, relief printing, intaglio printing, planographic printing, etc., may be employed.

In the case where the panel-type input device 10 is configured as a touch panel, the first electrode plate 16 having the first substrate 12 formed, e.g., from a glass plate is provided as a large-sized partly-finished component, and a plurality of dot spacers 44 are formed on the surface of the first conductive coat 14 thereof in a predetermined dispersed arrangement by, e.g., screen printing (step P3). On the other hand, the second electrode plate 22 having the second substrate 18 formed from a transparent resin film is provided through a cutting to have a predetermined workpiece size (step P4), and is subjected to an annealing process so as to remove the distortion of the film (step P5).

Next, a mask 56 having a shielding portion 52 and a transmitting portion 54 is set or placed over the first conductive coat 14 of the first electrode plate 16 and the second conductive coat 20 of the second electrode plate 22 as a sequential operation or a simultaneous parallel operation. Then, through the transmitting portion 54 of the mask 56, each of the conductive coats 14, 20 is exposed to a resistivity changing element 58 capable of changing the surface resistivity of the conducting polymer. In this connection, ultraviolet light (excimer UV, laser light, etc.), or alternatively, a conductivity controlling agent containing either one of an oxidizing substance and a basic substance, may be used as the resistivity changing element 58. The specific examples of the resistivity changing element 58 will be described later. The resistivity changing element 58 acts to increase a surface resistivity of one region of the conductive coat 14, 20 corresponding to the transmitting portion 54 of the mask 56 to an extent higher than a surface resistivity of another region of the conductive coat 14, 20 corresponding to the shielding portion 52. As a result, a detecting area 36 and an inoperative area 38 are formed in each of the first and second conductive coats 14, 20 of the first and second electrode plates 16, 22 (these processes are shown as insulator formation steps P6 and P7).

Next, a parallel electrode pair 24, 26 and conductors 28, 30 are formed at predetermined positions in the detecting area 36 and inoperative area 38 of each of the conductive coats 14, 20 into predetermined patterns by, e.g., screen printing using a silver (Ag) paste (steps P8 and P9). Then, for the first electrode plate 16 having the first substrate 12 formed, e.g., from a glass plate, an insulating layer 40 (FIG. 4) adapted to spatially insulate the conductors 28 from each other as well as the conductors 28 from the conductive coat 14, is formed into a predetermined pattern by, e.g., screen printing (step P10). In this connection, prior to the patterning of the silver paste, an insulating layer for preventing a silver ion migration may be formed in the inoperative area 38 of each conductive coat 14, 20 (FIG. 4). On the other hand, the second electrode plate 22 having the second substrate 18 formed from a transparent resin film is punched out into the shape of a finished product (step P11).

Next, the first electrode plate 16 and the second electrode plate 22 are assembled with each other in a predetermined relative arrangement as already described, and are adhered and fixed to each other with an adhesive layer 34 (step P12). Then, the first electrode plate 16 having the first substrate 12 formed, e.g., from a glass plate is shaped into a finished product by laser scribing, etc. (step P13). A connector 32 (FIG. 1) formed from a flexible printed circuit board (FPC), etc., is then connected to the conductors 28, 30 of the first and second electrode plates 16, 22 (step P14), and an electrical conduction test is carried out (step P15), so that the panel-type input device 10 is completed.

In the panel-type input device 10 having the above-described configuration, it is possible to form the detecting area 36 and the inoperative area 38 simply by exposing the conductive coats 14, 20 of the first and second electrode plates 16, 22 to the resistivity changing element 58 through the mask 56, while utilizing the special characteristics of the conducting polymer. Thus, it is not necessary to carry out a process of forming an insulating region on the substrate of a conventional panel-type input device, i.e., a process of coating or printing an insulating material or a process of locally removing a conductive coat. Therefore, in the panel-type input device 10, it is possible to reduce a panel thickness and to form an insulating region at a desired position with a desired pattern on the substrate at low cost.

In particular, the panel-type input device 10 can be embodied as an analog-system based resistive-type touch panel having a relatively simple and inexpensive configuration. In this configuration, the coating or printing of an insulating material or the local removal of a conductive coat is not carried out. Therefore, it is possible to eliminate drawbacks such that a boundary line between the detecting area 36 and the inoperative area 38 may be visible or the detecting area 36 and the inoperative area 38 may be visually distinguishable, and thus to improve the visibility of a display screen through the panel-type input device 10. In this connection, the inoperative area 38 having a surface resistivity increased by the function of the resistivity changing element 58 possesses an external appearance that cannot be easily distinguished from adjacent detecting area 36. Moreover, an electronic apparatus 59 (FIG. 2) with the panel-type input device 10 mounted on the screen of the display unit 46 has a low profile configuration due to the panel-type input device 10 with reduced thickness, and can be manufactured at low cost.

Figure 7:
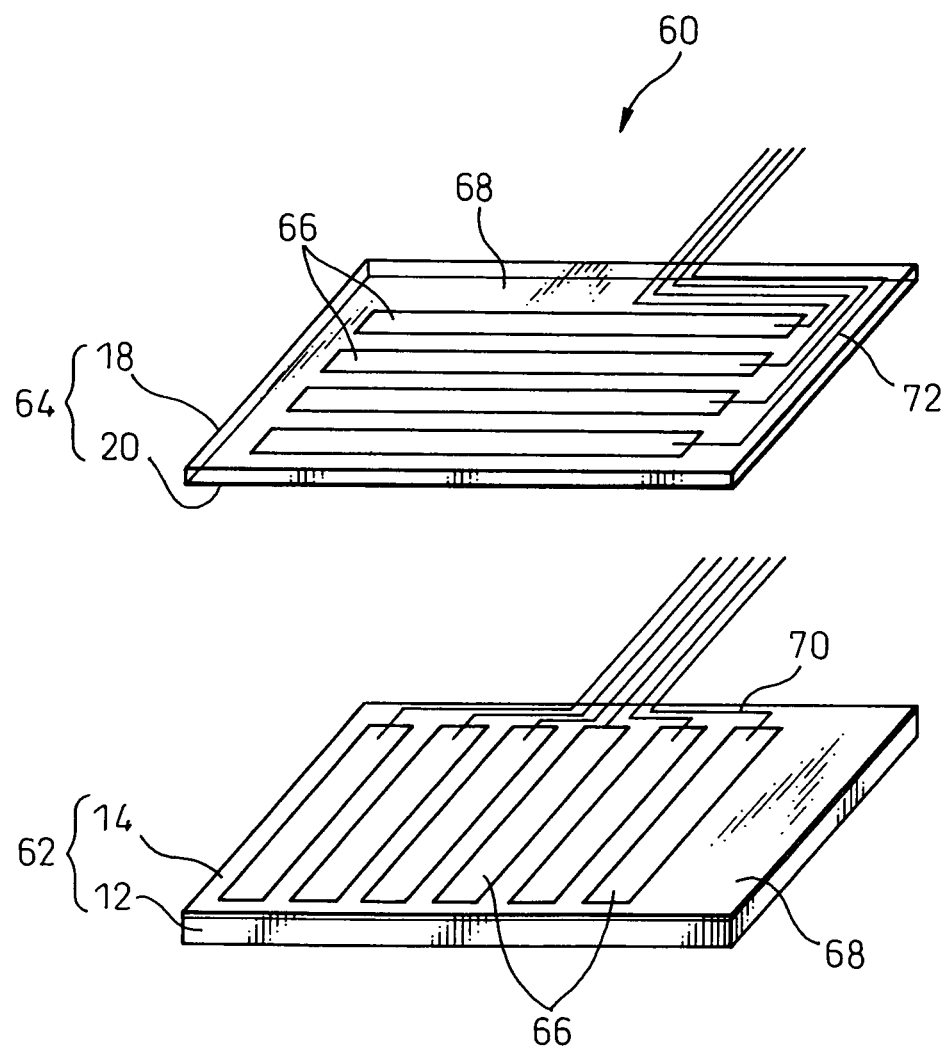
FIG. 7 is an exploded perspective view schematically showing a panel-type input device according to a second embodiment of the present invention.

FIG. 7 schematically shows a panel-type input device 60 according to a second embodiment of the present invention. The panel-type input device 60 has a configuration applicable to a digital-system based resistive-type touch panel, which is similar to the configuration of the above-described panel-type input device 10, except for the configuration of a conductive coat on a substrate. Thus, the corresponding components are denoted by common reference numerals, and explanation thereof is not repeated.

The panel-type input device 60 includes a first electrode plate 62 having a first substrate 12 and a first conductive coat 14, and a second electrode plate 64 having a second substrate 18 and a second conductive coat 20. Each of the first and second conductive coats 14, 20 of the first and second electrode plate 62, 64 is formed by using a conducting polymer. The first and second electrode plates 62, 64 are assembled with each other in a relative arrangement such that the conductive coats 14, 20 thereof are opposed to and spaced from each other while permitting a conductive contact therebetween, and are fixed together by a not-shown adhesive layer.

Each of the first and second conductive coats 14, 20 of the first and second electrode plates 62, 64 includes a plurality of detecting areas 66 adapted to detect a touch input and an inoperative area 68 disposed adjacent to the detecting areas 66, the inoperative area 68 having a surface resistivity higher than a surface resistivity of the plurality of detecting areas 66. In each of the first and second conductive coats 14, 20 of the first and second electrode plates 62, 64, the detecting areas 66 have rectangular strip-shaped profiles generally identical to each other, and are disposed at regular intervals and extend parallel to each other. The inoperative area 68 includes a portion extending in the shape of a rectangular or picture frame along the outer edge of each conductive coat 14, 20, and strip-shaped portions interposed between adjacent detecting areas 66 and insulating the detecting areas 66 from each other. A plurality of conductors 70, 72 individually connected to the respective detecting areas 66 are formed in the rectangular frame portion of the inoperative area 68 of each of the first and second conductive coats 14, 20 of the first and second electrode plates 62, 64. Once the first and second electrode plates 62, 64 are properly assembled with each other, respective sets of the plurality of detecting areas 66 of the conductive coats 14, 20 of the electrode plates 62, 64 extend in directions orthogonal to each other.

The panel-type input device 60 operates, under the control of a control circuit (not shown), by applying a predetermined voltage to the detecting areas 66 of the conductive coats 14, 20 of the first and second electrode plates 62, 64. In this state, at the instant when an operator presses a desired point on the outer surface of, e.g., the second substrate 18 of the second electrode plate 64 with a pen or a finger, etc. (i.e., performs a touch input), provided that the pressed point is included in an intersection of the detecting areas 66 of the conductive coats 14, 20, the respective detecting areas 66 of the conductive coats 14, 20, intersecting with each other, come into conductive contact with each other at the intersection (or the pressed point). A processing section (not shown) provided in the control circuit determines the position of the pressed point (i.e., the position of the intersection of the detecting areas 66) based on the identification of a pair of detecting areas 66 at which electric current is generated due to the conductive contact, and thereby detects an ON-input at the pressed point.

The panel-type input device 60 can be manufactured by a manufacturing method similar to that of the panel-type input device 10. In this connection, the arrangement, shapes and dimensions of shielding portion 52 and transmitting portion 54 of a mask 56, adapted to be used in the manufacturing method for the panel-type input device 60, are determined correspondingly to the detecting areas 66 and inoperative area 68 required in the panel-type input device 60.

In the panel-type input device 60, it is also possible, similar to the panel-type input device 10, to reduce a panel thickness and to form an insulating region at a desired position with a desired pattern on the substrate at low cost. In particular, the panel-type input device 60 can be embodied as a digital-system based resistive-type touch panel having a relatively simple and inexpensive configuration, wherein the first electrode plate 62 is used as a lower-side electrode plate, the first substrate 12 thereof being formed from a transparent glass or resin plate or a transparent resin film and the first conductive coat 14 being formed from a transparent conducting polymer, and wherein the second electrode plate 64 is used as an upper-side electrode plate, the second substrate 18 thereof being formed from a transparent resin film with high flexibility and the second conductive coat 20 being formed from a transparent conducting polymer. In this configuration, it is possible to eliminate drawbacks such that a boundary line between the detecting areas 66 and the inoperative area 68 may be visible or the detecting areas 66 and the inoperative area 68 may be visually distinguishable, and thus to improve the visibility of a display screen through the panel-type input device 60.

Further, similar to the panel-type input device 10, an electronic apparatus 59 (FIG. 2) with the panel-type input device 60 mounted on the screen of the display unit 46 has a low profile configuration due to the panel-type input device 60 with reduced thickness, and can be manufactured at low cost. Moreover, in the case of the panel-type input device 60 configured as a touch panel, similar to the panel-type input device 10, the second substrate 18 made of a transparent resin film may be formed from a PET film having ultraviolet protection properties, and/or an auxiliary functional layer (not shown) optionally provided on the outer surface of the second substrate 18 may be formed from a material having ultraviolet protection properties, so that it is possible to manufacture a touch panel possessing excellent resistance to ultraviolet radiation, which can protect the first and second conductive coats 14, 20 (especially, the detecting areas 66 thereof)

against ultraviolet radiation such as sunlight during use of a finished product of the touch panel.

Figure 8:
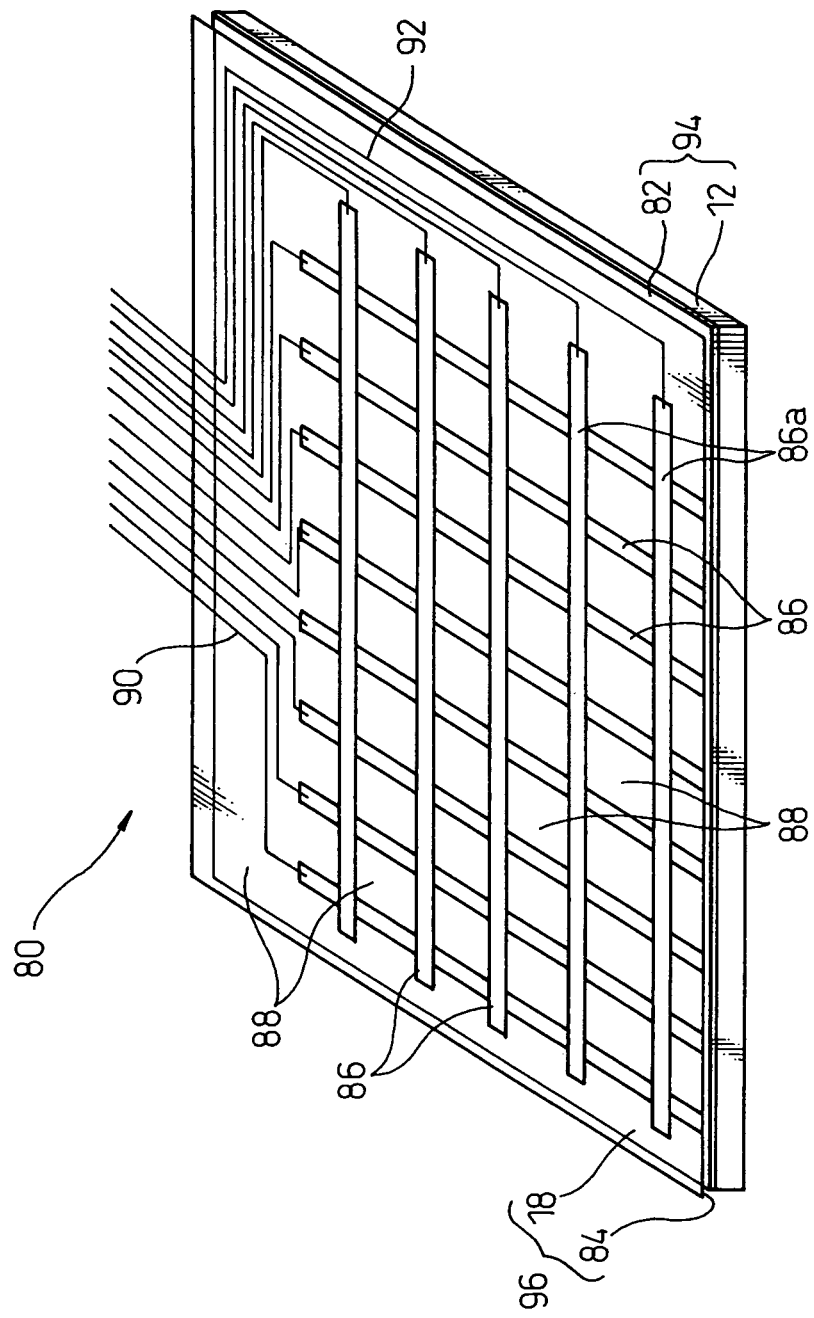
FIG. 8 is a perspective view schematically showing a panel-type input device according to a third embodiment of the present invention.

FIG. 8 schematically shows a panel-type input device 80 according to a third embodiment of the present invention. The panel-type input device 80 has a configuration applicable to a projected-capacitive-system based capacitive-type touch panel, which is similar to the configuration of the panel-type input device 10, except for the configuration of a conductive coat and a coordinate detection system. Thus, the corresponding components are denoted by common reference numerals, and explanation thereof is not repeated.

The panel-type input device 80 includes a first conductive coat 82 and a second conductive coat 84, disposed oppositely to and insulated from each other. Each of the first and second conductive coats 82, 84 is formed by using a conducting polymer. In the illustrated embodiment, the first and second conductive coats 82, 84 are provided on mutually opposed surfaces of a pair of substrates (i.e., first and second substrates) 12, 18 disposed oppositely to each other. An insulating layer (not shown) prepared as a separate member is interposed entirely between the mutually opposing first and second conductive coats 82, 84. As an alternative configuration, the first and second conductive coats 82, 84 may be provided on opposite surfaces of a single substrate 12. In the alternative configuration, a protective sheet formed from a PET film having ultraviolet protection properties may be secured on one of the conductive coats 82, 84 arranged at a touch input side.

Each of the first and second conductive coats 82, 84 includes a plurality of detecting areas 86 adapted to detect a touch input and an inoperative area 88 disposed adjacent to the detecting areas 86, the inoperative area 88 having a surface resistivity higher than a surface resistivity of the plurality of detecting areas 86. In each of the first and second conductive coats 82, 84, the detecting areas 86 have rectangular strip-shaped profiles generally identical to each other, and are disposed at regular intervals and extend parallel to each other. The inoperative area 88 includes a portion extending in the shape of a rectangular or picture frame along the outer edge of each conductive coat 82, 84, and strip-shaped portions interposed between adjacent detecting areas 86 and insulating the detecting areas 86 from each other. A plurality of conductors 90, 92 individually connected to the respective detecting areas 86 are formed in the rectangular frame portion of the inoperative area 88 of each of the first and second conductive coats 82, 84. Once the first and second conductive coats 82, 84 are disposed in a proper relative arrangement, respective sets of the plurality of detecting areas 86 of the conductive coats 82, 84 extend in directions orthogonal to each other.

The panel-type input device 80 operates, under the control of a control circuit (not shown), by applying a predetermined voltage to the detecting areas 86 of the first and second conductive coats 82, 84. In this state, at the instant when an operator touches a desired point on, e.g., the second substrate 18 with a finger (i.e., performs a touch input), an electric current is generated at the touched point, and resultant electric currents pass through the detecting areas 86 of the first and second conductive coats 82, 84 correspondingly to distances from the tip of the finger (an electrostatic capacity in the intersections 86a of the detecting areas 86 of the conductive coats 82, 84 at the touching point changes correspondingly to distances from the tip of the finger). A processing section (not shown) provided in the control circuit determines the position of the touched point based on the identification of the detecting areas 86 through which electric currents pass correspondingly to the distances from the touched point due to the touch input (based on the identification of a pair of detection areas 86 generating a capacity change between the conductive coats 82, 84 due to the touch input and the amount of change in the electrostatic capacity), and thereby detects two-dimensional coordinate of the touched point.

Figure 9:
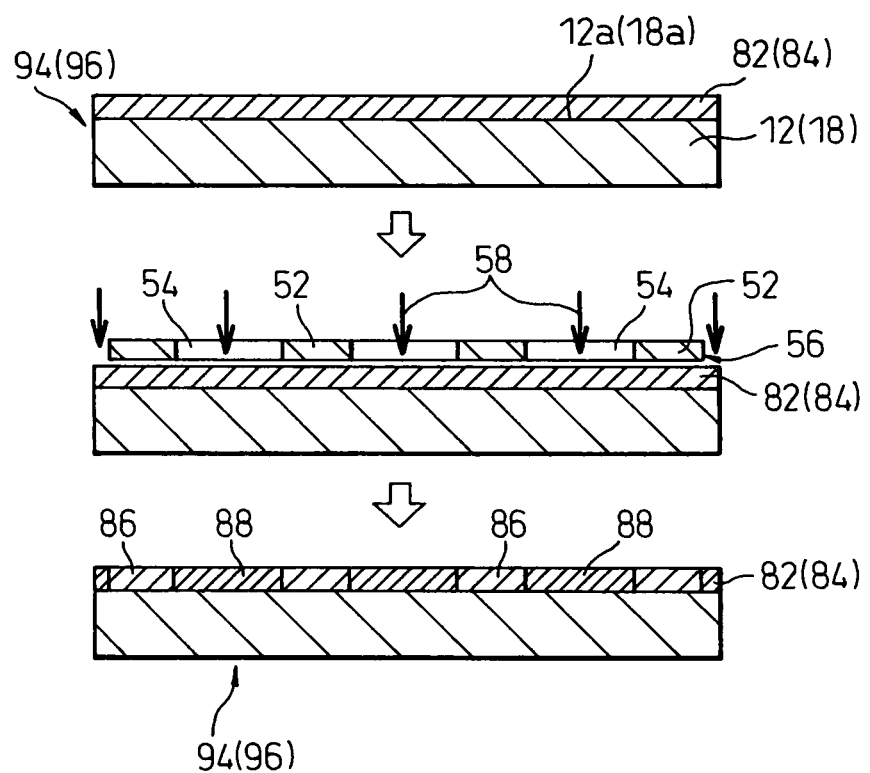
FIG. 9 is an illustration for explaining major steps of a manufacturing method, according to another embodiment of the present invention, for manufacturing the panel-type input device shown in FIG. 8.
Figure 10:
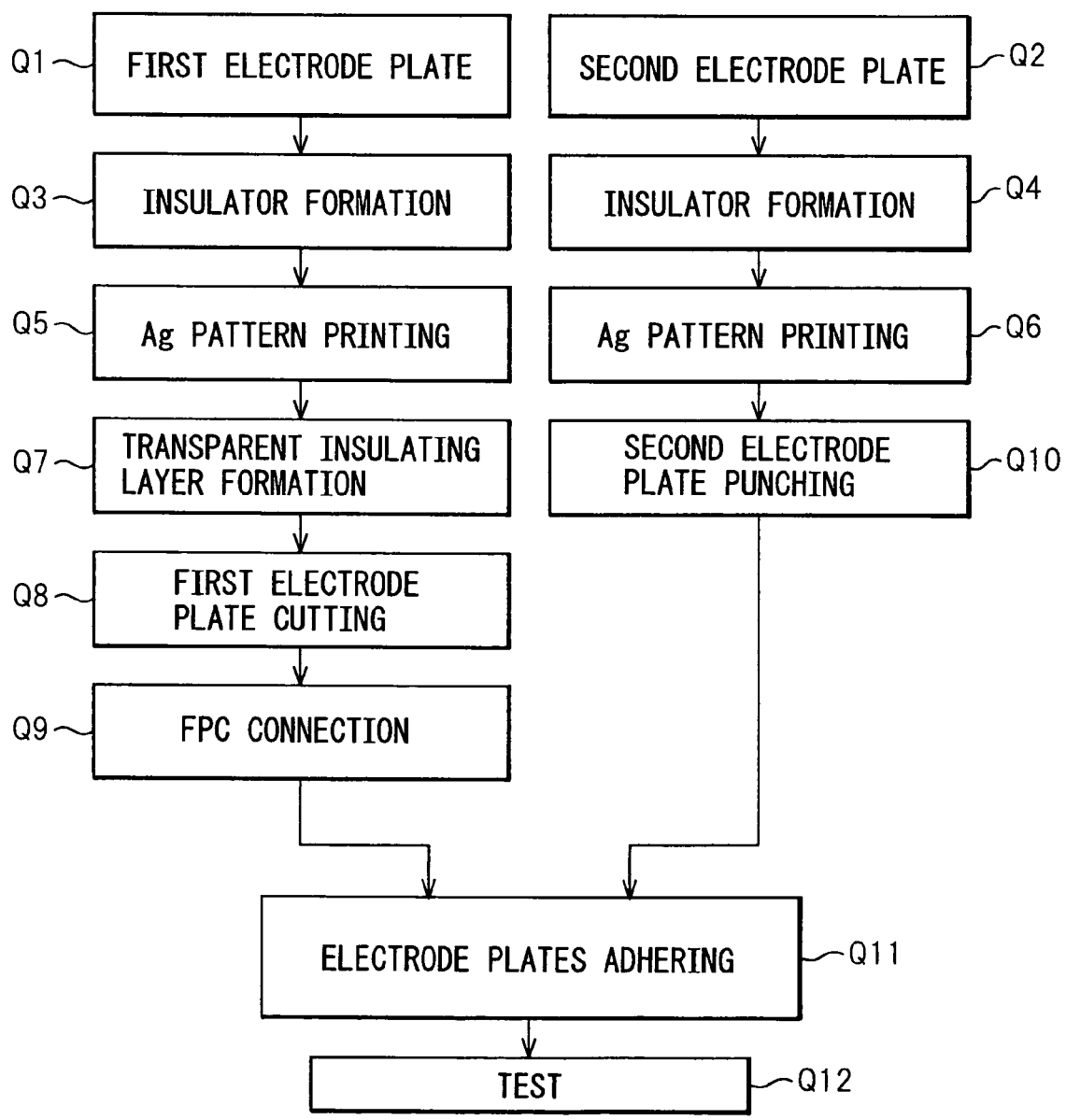
FIG. 10 is a flow chart showing the manufacturing method and including the steps shown in FIG. 9.

An exemplary method for manufacturing the panel-type input device 80 will be described below with reference to the schematic view of FIG. 9 and the flow chart of FIG. 10. First, a first electrode plate 94 with a first conductive coat 82 formed or laminated on the surface 12a of a first substrate 12 and a second electrode plate 96 with a second conductive coat 84 formed or laminated on the surface 18a of a second substrate 18 are provided (steps Q1 and Q2). In the case where the panel-type input device 80 is configured as a touch panel, similar to the exemplary manufacturing method of the panel-type input device 10, the first electrode plate 94 (a partly-finished component) having the first substrate 12 formed, e.g., from a glass plate, and the second electrode plate 96 (a partly-finished component) having the second substrate 18 formed, e.g., from a transparent resin film, are provided. Process of forming the conductive coats 82, 84 made of a conducting polymer is pursuant to that in the manufacturing method of the panel-type input device 10.

Next, a mask 56 having a shielding portion 52 and a transmitting portion 54 is set or placed over the first conductive coat 82 and the second conductive coat 84 as a sequential operation or a simultaneous parallel operation. Then, through the transmitting portion 54 of the mask 56, each of the conductive coats 82, 84 is exposed to a resistivity changing element 58 (ultraviolet light (excimer UV, laser light, etc.) or a conductivity controlling agent) that can change the surface resistivity of the conducting polymer. The resistivity changing element 58 acts to increase a surface resistivity of one region of the conductive coat 82, 84 corresponding to the transmitting portion 54 of the mask 56 to an extent higher than a surface resistivity of another region of the conductive coat 82, 84 corresponding to the shielding portion 52. As a result, detecting areas 86 and an inoperative area 88 are formed in each of the first and second conductive coats 82, 84 (these processes are shown as insulator formation steps Q3 and Q4).

Next, a plurality of conductors 90, 92 are formed at predetermined positions in the inoperative area 86 of each of the conductive coats 82, 84 into predetermined patterns by, e.g., screen printing using a silver (Ag) paste (steps Q5 and Q6). Then, an insulating layer (a transparent insulating layer, in an application as a touch panel) is formed entirely on the surface of the first conductive coat 82 (step Q7). Then, the first electrode plate 94 having the first substrate 12 formed, e.g., from a glass plate is shaped into a finished product by laser scribing, etc. (step Q8), and a connector (not shown) formed from a flexible printed circuit board (FPC), etc., is then connected to the conductors 90 (step Q9). On the other hand, the second electrode plate 96 having the second substrate 18 formed from a transparent resin film is punched out into the shape of a finished product (step Q10). Next, the first electrode plate 94 and the second electrode plate 96 are assembled with each other in a predetermined relative arrangement in which the respective sets of detecting areas 86 orthogonally intersect with each other, and the entire surfaces of mutually opposing conductive coats 82, 84 are adhered and fixed to each other with an adhesive layer (a transparent adhesive layer, in an application as a touch panel) (step P11). At this time, the conductor 92 formed on the second electrode plate 96 is connected to the connector. Then, an electrical conduction test is carried out (step Q12), so that the panel-type input device 80 is completed.

In the panel-type input device 80 having the above configuration, it is also possible, similar to the panel-type input device 10, to reduce a panel thickness and to form an insulating region at a desired position with a desired pattern on the substrate at low cost. In particular, the panel-type input device 80 can be embodied as a projected-capacitive-system based capacitive-type touch panel having an excellent transparency and durability, wherein the first electrode plate 94 is used as a lower-side electrode plate with the first substrate 12 thereof being formed from a transparent glass or resin plate or a transparent resin film and the first conductive coat 82 being formed from a transparent conducting polymer, and wherein the second electrode plate 96 is used as an upper-side electrode plate with the second substrate 18 thereof being formed from a transparent resin film with high flexibility and the second conductive coat 84 being formed from a transparent conducting polymer. In this configuration, it is possible to eliminate drawbacks such that a boundary line between the detecting areas 86 and the inoperative area 88 may be visible or the detecting areas 86 and the inoperative area 88 may be visually distinguishable, and thus to improve the visibility of a display screen through the panel-type input device 80.

Further, similar to the panel-type input device 10, an electronic apparatus 59 (FIG. 2) with the panel-type input device 80 mounted on the screen of the display unit 46 has a low profile configuration due to the panel-type input device 80 with reduced thickness, and can be manufactured at low cost. Moreover, in the case of the panel-type input device 80 configured as a touch panel, similar to the panel-type input device 10, the second substrate 18 made of a transparent resin film may be formed from a PET film having ultraviolet protection properties, and/or an auxiliary functional layer (not shown) optionally provided on the outer surface of the second substrate 18 may be formed from a material having ultraviolet protection properties, so that it is possible to manufacture a touch panel possessing excellent resistance to ultraviolet radiation, which can protect the first and second conductive coats 82, 84 (especially, the detecting areas 86 thereof) against ultraviolet radiation such as sunlight during use of a finished product of the touch panel.

FIG. 11 shows a configuration of first and second electrode plates 94, 96 as a modification of the panel-type input device 80. In this modification, an auxiliary conductive layer 98 formed from an inorganic conducting substance (e.g., indium tin oxide (ITO), gold (Au), carbon nanotube, etc.) is provided between the plurality of detecting areas 86 formed in each of the first and second conductive coats 82, 84 and the mutually opposing surfaces 12a, 18a of the first and second electrode plates 12, 18, (FIG. 1C). The auxiliary conductive layer 98 is formed on the surface 12a, 18a of each of the first and second electrode plates 12, 18 as a thin film with patterns generally identical to the patterns of the detecting areas 86 of each conductive coat 82, 84 through, e.g., a process similar to a process for forming an ITO coat (i.e., a coat-forming technology) in a conventional touch panel. As an alternative configuration, the auxiliary conductive layer 98 may be provided between the plurality of detecting areas 86 of a pair of conductive coats 82, 84 and the opposite surfaces of a single substrate 12.

In the configuration of the illustrated modification, the electrical conductivity of the plurality of detecting areas 86 of the first and second conductive coats 82, 84 is substantially improved (i.e., the surface resistivity of the detecting areas 86 is lowered) by the electrical conducting function of the auxiliary conductive layer 98 contacting generally entirely the detecting areas 86. Therefore, the configuration of the modification is particularly advantageous in the case where each detecting area 86 is formed with a relatively narrow strip-shaped pattern (e.g., in the case where the panel-type input device 80 is used as a projected-capacitive-system based capacitive-type touch panel), since it is possible to prevent the conductivity of the detecting areas 86 formed from a conducting polymer from being deteriorated due to their own shapes (or prevent the surface resistivity from increasing).

Figure 11A:
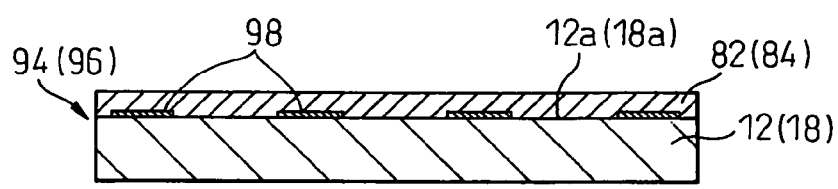
FIGS. 11A to 11C are illustrations showing the modified configuration of the panel-type input device shown in FIG. 8, and explaining major steps of the manufacturing method thereof.

The panel-type input device 80 including the first and second electrode plates 94, 96 according to the illustrated modification can be manufactured through a procedure generally identical to that of the manufacturing method described with reference to FIGS. 9 and 10. More specifically, the first and second electrode plates 94, 96 (partly-finished components) are first provided by forming or laminating a plurality of auxiliary conductive layers 98 on the surfaces 12a, 18a of the first and second substrate 12, 18 in a pattern generally identical to a finally-obtainable objective pattern of detecting areas 86, and by forming the first and second conductive coats 82, 84 so as to cover the auxiliary conductive layers 98 (FIG. 11A). In this connection, each of the first and second conductive coats 82, 84 formed through coating or printing have a thickness sufficiently larger than a thickness of the auxiliary conductive layers 98 formed through a coat-forming technology, the surface of each of the first and second conductive coats 82, 84 becomes generally flat.

Figure 11B:
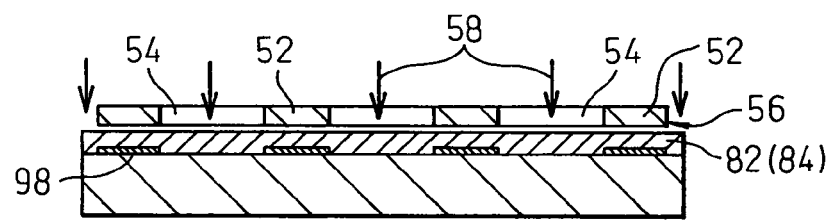
Figure 11C:
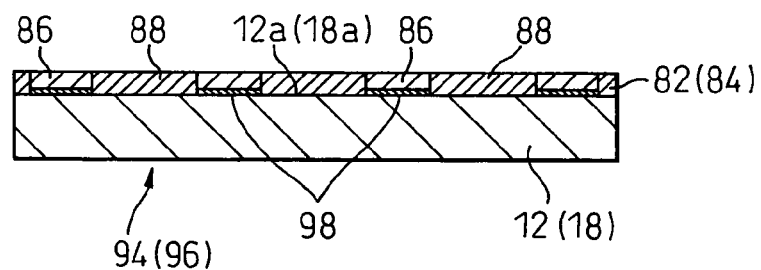

Next, a mask 56 having a shielding portion 52 and a transmitting portion 54 is set or placed over the first conductive coat 82 and the second conductive coat 84 as a sequential operation or a simultaneous parallel operation, at a position where the shielding portion 52 oppositely faces the auxiliary conductive layers 98 with their profiles being aligned to each other. Then, through the transmitting portion 54 of the mask 56, each of the conductive coats 82, 84 is exposed to a resistivity changing element 58 (ultraviolet light (excimer UV, laser light, etc.) or a conductivity controlling agent) that can change the surface resistivity of the conducting polymer, so as to increase a surface resistivity of one region of the conductive coat 82, 84 corresponding to the transmitting portion 54 of the mask 56 to an extent higher than a surface resistivity of another region of the conductive coat 82, 84 corresponding to the shielding portion 52 (FIG. 11B). As a result, detecting areas 86 superimposed on the auxiliary conductive layers 98 and an inoperative area 88 surrounding the detecting areas 86 are formed in each of the first and second conductive coats 82, 84 (FIG. 11C).

In each of the first and second electrode plates 94, 96 fabricated through the above steps, the auxiliary conductive layers 98 locally formed on the surface 12a, 18a of the first or second substrate 12, 18 are covered entirely by the first or second conductive coat 82, 84 together with a part of the surface 12a, 18a surrounding the auxiliary conductive layers 98, so that, even if the first and second electrode plates 94, 96 are transparent, the auxiliary conductive layers 98 are not highly visible. Therefore, the modified panel-type input device 80 used as a touch panel and manufactured by using the modified first and second electrode plates 94, 96 has advantages such that a boundary line between the detecting areas 86 (including the auxiliary conductive layers 98) and the inoperative area 88 is not visible, and the detecting areas 86 and the inoperative area 88 cannot be visually distinguished, and thus the visibility of a display screen through the panel-type input device 80 is improved.

The panel-type input device 10, 60, 80 according to the preferred embodiments of the present invention may be configured such that the conducting polymer forming the first conductive coat 14, 82 and the second conductive coat 20, 84 contains an additive adapted to be denatured into either one of an oxidizing substance and a basic substance by light irradiation (especially, ultraviolet light irradiation). According to this configuration, in the above-described manufacturing method, simply by irradiating each conductive coat 14, 20, 82, 84 with light (especially, ultraviolet light) through the transmitting portion 54 of the mask 56, instead of using a conductivity controlling agent containing either one of an oxidizing substance and a basic substance as the resistivity changing element 58, it is possible to more rapidly form the inoperative area 38, 68, 88 in a desired pattern on the conductive coat 14, 20, 82, 84 due to a resistivity changing function equivalent to the function of the conductivity controlling agent.

In the above configuration, various organic peroxides such as benzoyl peroxide, 1-butyl peroxide, dicumyl peroxide, etc., may be used as an additive adapted to be denatured into an oxidizing substance by light irradiation. On the other hand, as an additive adapted to be denatured into a basic substance by light irradiation, the following materials may be used: triphenyl methanol; carbamates such as benzyl carbamate, benzoin carbamate, etc.; amides such as o-carbamoyl hydroxylamide, o-carbamoyl oxim, aromatic sulfonamide, alpha-lactum and N-(2-allylethynyl)amide, or other amides; oxim ester; α-aminoacetophenon; cobalt complex, etc. In particular, it is preferred to use 2-nitrobenzyl cyclohexyl carbamate, triphenyl methanol, o-carbamoyl hydroxylamide, o-carbamoyl oxim, [[(2,6-dinitrobenzyl)oxy]carbonyl]cyclohexyl amine, bis[[(2-nitrobenzyl)oxy]carbonyl]hexane-1, 6-diamine, 4-(methylthio benzoyl)-1-methyl-1-morpholinoethane, (4-morpholinobenzoyl)-1-benzyl-1-dimethylamino propane, N-(nitrobenzyloxy carbonyl) pyrrolidine, hexanmine cobalt (III) tris (triphenyl methylborate), 2-benzyl-2-dimethylamino-1-(4-morpholinophenyl)-butanone, etc.

In order to further clarify the effect of the panel-type input device according to the present invention, the contents of experiments performed by inventors will be described below with reference to FIGS. 12 and 13.

[Experiment 1]

As a sample of the electrode plate 16, 22 of the panel-type input device 10, an electrode plate (50 mm×60 mm) having a configuration in which a conductive coat (100 nm in thickness) formed from polythiophene-based conducting polymer (PEDOT/PSS) was coated onto a substrate (188 μm in thickness) formed from a PET film was prepared. The initial surface resistivity (pursuant to, e.g., JIS K6911) of the conductive coat of this electrode plate was 653Ω/□ (ohm/square). Then, the electrode plate was irradiated with ultraviolet light with 365 nm peak-wavelength including 245 nm wavelength and 1000 mW/cm² irradiance, from a high-pressure mercury lamp, in the atmosphere containing 0.1 ppm-100 ppm ozone, in a direction vertical to the surface of the conductive coat, at a scan speed of 0.67 m/min, by using an ultraviolet light irradiator UVC-02516 (manufactured by USHIO Inc., Tokyo, Japan). The irradiance light quantity of ultraviolet light irradiated in a single scan (referred to as a unit light quantity) was 3856 mJ/cm². FIG. 12 shows a mode of change in the surface resistivity of the conductive coat, measured through the repeated irradiation of the unit light quantity. FIG. 13 shows the spectral distribution of the ultraviolet light used in experiment 1.

Figure 12:
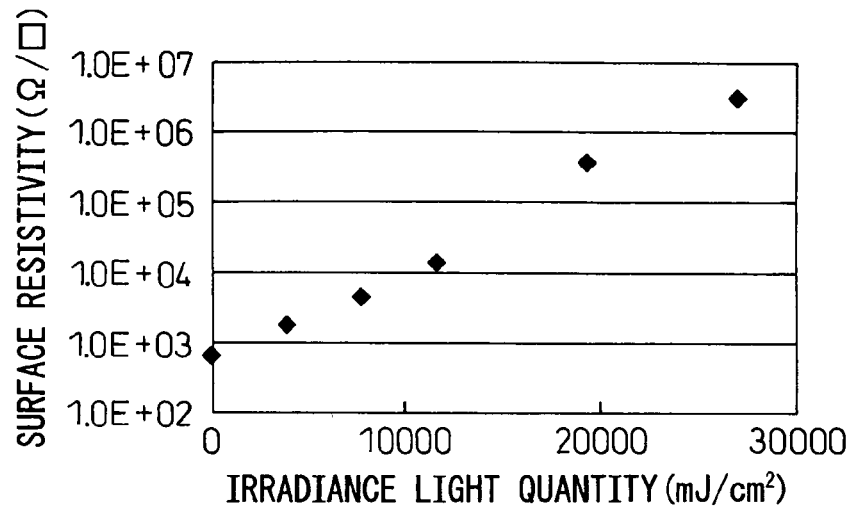
FIG. 12 is an illustration showing a mode of change in the surface resistivity of a conductive coat due to ultraviolet light irradiation.
Figure 13:
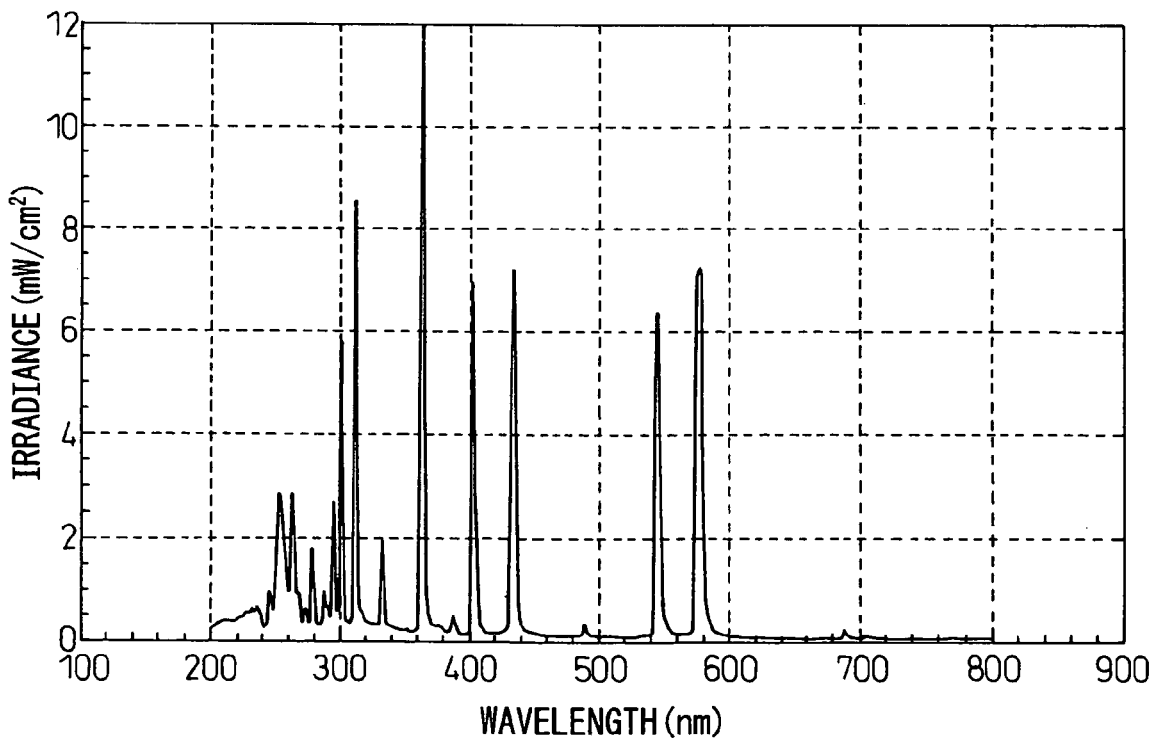
FIG. 13 is an illustration showing the spectral distribution of ultraviolet light used in an experiment, the result of which is shown in FIG. 12.

As shown in FIG. 12, it has been proved that the surface resistivity of the conductive coat is increased by the irradiation of ultraviolet light. In this connection, there is no practical problem in the conductive coat 14, 20 of the electrode plate 16, 22 of the panel-type input device 10 as long as the surface resistivity of the inoperative area 38 is at least ten times the surface resistivity of the detecting area 36. Therefore, it will be understood from FIG. 12 that the first and second electrode plates 16, 22 can be successfully manufactured by irradiating, through the mask 56 (FIG. 5), the first and second conductive coats 14, 20 with ultraviolet light with at least 12000 mJ/cm² irradiance.

[Experiment 2]

Figure 14:
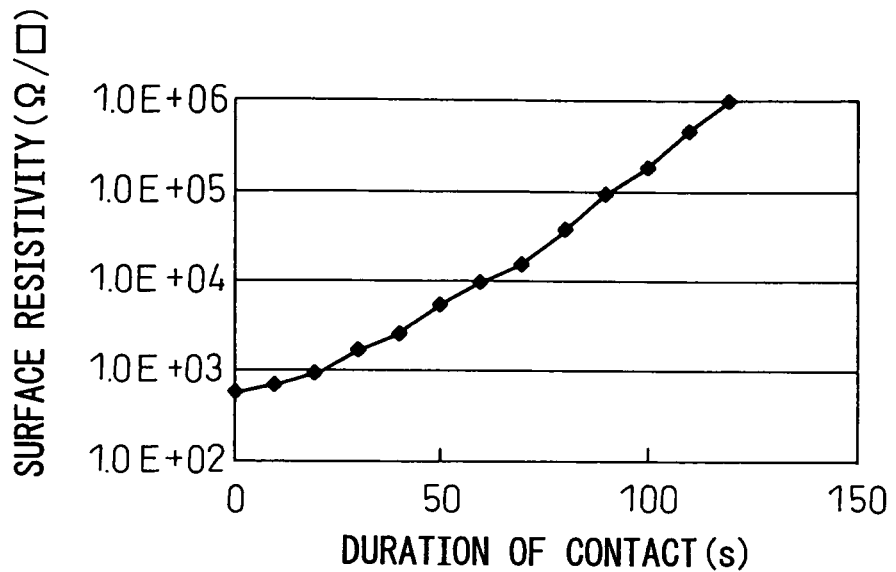
FIG. 14 is an illustration showing a relationship between the surface resistivity of a conductive coat and the duration of contact with a basic reagent.

In relation to the aforementioned sample of the electrode plate, a conductivity controlling agent selected from a group including an oxidizing reagent such as hypochlorous acid, chloric acid, nitric acid, nitrous acid, sulfuric acid, sulfurous acid, etc., and a basic reagent such as sodium hydroxide, potassium, ammonium, tetraethylammonium hydroxide, etc., was contacted with the conductive coat through the mask 56 (FIG. 5), so as to increase the surface resistivity of the desired region of the conductive coat. As a result, two regions having mutually different surface resistivity were successfully formed in the conductive coat, which can be used as the conductive coats 14, 20 of the electrode plates 16, 22 of the panel-type input device 10. In particular, a basic reagent containing 10% sodium hydroxide solution as a major component was excellent in a resistivity increasing function, and the surface resistivity of the desired region of the conductive coat was necessarily and sufficiently increased by contacting the conductive coat with such basic reagent for at least 60 seconds. FIG. 14 shows a relationship between the surface resistivity of the conductive coat and the duration of contact with the basic reagent containing 10% sodium hydroxide solution.

[Experiment 3]

Figure 15:
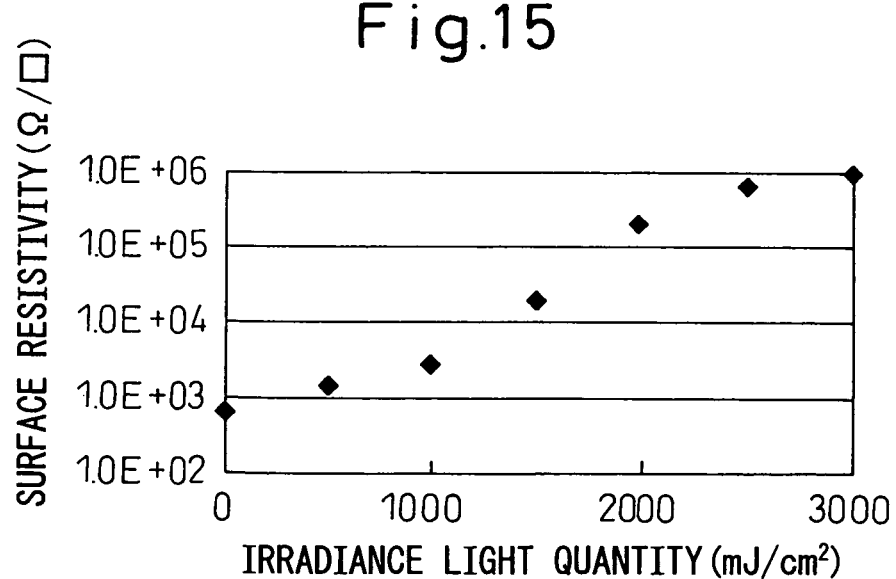
FIG. 15 is an illustration showing a mode of change in the surface resistivity of a conductive coat due to ultraviolet light irradiation.

The aforementioned sample of the electrode plate was prepared by modifying the conductive coat so as to be formed from polythiophene-based conducting polymer (PEDOT/PSS) containing 3% benzoyl peroxide. The initial surface resistivity (pursuant to, e.g., JIS K6911) of the conductive coat of this electrode plate was 698Ω/□ (ohm/square). Then, the electrode plate was irradiated with ultraviolet light with 365 nm peak wavelength and 1000 mW/cm² irradiance, from a high-pressure mercury lamp, in a direction vertical to the surface of the conductive coat, at a scan speed of 5 m/min, by using the same apparatus as in Experiment 1. The irradiance light quantity of ultraviolet light in a single scan (referred to as a unit light quantity) was 500 mJ/cm². FIG. 15 shows a mode of change in the surface resistivity of the conductive coat, measured through the repeated irradiation of the unit light quantity. As shown in FIG. 15, it has been proved that the surface resistivity of the conductive coat is increased by the irradiation of ultraviolet light.

While the invention has been described with reference to specific preferred embodiments, it will be understood by those skilled in the art that various changes and modifications may be made thereto without departing from the scope of the following claims.

The invention claimed is:

1. A panel-type input device comprising:
a pair of electrode plates, each electrode plate having a substrate and a conductive coat provided on a surface of said substrate, said conductive coat of said each electrode plate being formed from a polymer, said pair of electrode plates being assembled with each other in a relative arrangement such that conductive coats of said electrode plates are facing and spaced from each other while permitting a conductive contact between said conductive coats, said conductive coat of said each electrode plate being divided into a detecting area so that a touch input can be detected, and an inoperative area located around said detecting area and having a surface resistivity higher than a surface resistivity of said detecting area;
pairs of electrodes, a first pair corresponding to said detecting area of said conductive coat of a first electrode plate and a second pair corresponding to said detecting area of said conductive coat of a second electrode plate, said electrodes of each pair being provided on a corresponding detecting area at opposing locations on the corresponding detecting area for applying a voltage to the corresponding detecting area; and conductors, each conductor being connected to one of said electrodes and formed on said inoperative area of said conductive coat of a respective electrode plate, wherein said each conductor is electrically isolated from said detecting area of the respective electrode plate.

2. The panel-type input device of claim 1, wherein said polymer forming said conductive coat contains an additive adapted to be denatured into either one of an oxidizing substance and a basic substance by ultraviolet light irradiation.

3. The panel-type input device of claim 1, wherein said pair of electrode plates are transparent.

4. An electronic apparatus comprising:

a display unit; and the panel-type input device of claim 3, said panel-type input device being mounted on a screen of said display unit.

* * * * *